United States Patent [19]

Yoder et al.

[11] Patent Number: 5,792,924
[45] Date of Patent: *Aug. 11, 1998

[54] BIOLOGICALLY SAFE PLANT TRANSFORMATION SYSTEM

[75] Inventors: John I. Yoder, Winters; Michael W. Lassner, Davis, both of Calif.

[73] Assignee: The Regents of the University of California, Oakland, Calif.

[ * ] Notice: The term of this patent shall not extend beyond the expiration date of Pat. No. 5,225,341.

[21] Appl. No.: 445,606

[22] Filed: May 22, 1995

Related U.S. Application Data

[63] Continuation of Ser. No. 77,787, Jun. 15, 1993, Pat. No. 5,482,852, which is a continuation-in-part of Ser. No. 555,271, Jul. 19, 1990, Pat. No. 5,525,341.

[51] Int. Cl.$^6$ .................. C12N 15/00; A01H 1/06
[52] U.S. Cl. .............. 800/205; 435/172.3; 435/320.1; 935/30; 935/64; 935/67
[58] Field of Search ................ 800/205; 435/172.3, 435/172.1; 536/24.1, 27.1; 47/58; 935/30, 64, 67

[56] References Cited

U.S. PATENT DOCUMENTS 5,015,580  5/1991  Christou et al. ............... 435/172.3
5,225,341  7/1993  Yoder et al. ................... 435/172.3

*Primary Examiner*—Gary Benzion
*Attorney, Agent, or Firm*—Townsend and Townsend and Crew

[57] ABSTRACT

This invention relates to methods for producing transgenic plants that contain a gene of interest and that are free of foreign ancillary nucleic acids. These methods allow for the production of plants which thus contain a desired gene, but which are free of vector sequences and/or marker sequences used to transform the plant. The method of transforming such plants calls for transforming the plants with a gene of interest by introduction of the gene on a DNA construct comprising a transposon and foreign ancillary nucleic acids; crossing the transformed plant through self-crossing or with another plant to obtain $F_1$ or more removed generation progeny; and utilizing a means for selecting those progeny that carry the gene of interest and are free of the ancillary nucleic acids. Such progeny may be detected biochemically, by Southern hybridization, through the use of polymerase chain reaction procedures and other methods available in the art.

3 Claims, 7 Drawing Sheets

*pMAC*

*pDS203*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:1:

CGCTCCTCAC AGGCTCATCT C                                                    21

( 2 ) INFORMATION FOR SEQ ID NO:2:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:2:

CCTCCGCAAA TCTTCGAACA G                                                    21

BIOLOGICALLY SAFE PLANT TRANSFORMATION SYSTEM

This application is a continuation of application Ser. No. 08/077,787, filed Jun. 15, 1993, now U.S. Pat. No. 5,482,852, which is a continuation-in-part of application Ser. No. 07/555,271, filed Jul. 19, 1990, now U.S. Pat. No. 5,225,341.

This invention was made with government support under Grant Nos. 86-CRCR-1-1991 and 88-37234-3665 awarded by the USDA and the Government has certain rights in this invention.

BACKGROUND OF THE INVENTION

This invention relates to methods for creating transgenic plants through the use of transposons. More specifically, it relates to a system that provides transformed plants that contain a minimum amount of ancillary foreign genetic material. In addition, methods are provided for molecular fingerprinting proprietary cultivars using transposons and other introduced DNA sequences.

The production of transgenic plants opens an exciting field with the promise that innumerable desirable characteristics may be incorporated into the plants society depends upon. For example, due to the environmental concerns and other costs incurred with the use of chemical pesticides, the ability to develop plants which are naturally resistant to pests is paramount.

Using current transformation procedures, however, only about one out of every one million plant cells is transformed. The problem of transformation then translates into identifying the single cell that has been transformed in this background of untransformed cells. This problem has been addressed generally by physically linking a gene, typically a bacterial gene that confers antibiotic resistance, to the desired gene. The cell that has taken up the desired gene can then be selected by its ability to grow on a medium containing the particular antibiotic. Untransformed plant cells do not contain the resistance gene and, thus, do not grow.

The presence of antibiotic resistance genes and other ancillary sequences in the final cultivar is particularly undesirable, however. These ancillary sequences are necessary for the transformation processes, but they do not positively contribute to the final cultivar and in fact lessen its desirability to the consumer. In the public perception, transfer of sequences between widely separated taxonomic groups is of greater concern than transfer between more closely related groups. Thus, a transgenic cultivar bearing sequences from a bacterium may be more objectionable than one bearing sequences from a wild species in the same genus. To increase public acceptance of transgenic plants, it is extremely important to eliminate bacterial resistance genes and other ancillary sequences from the cultivar. The biological effects of the insertion of this unwanted genetic material is unclear. Transgenic plants have thus been met with resistance and skepticism in large part because of the uncertainty associated with the ancillary genetic material.

The presence of these undesirable sequences may also complicate the regulatory procedures necessary to bring the cultivar to the market place. The current regulatory structure bases the degree of scrutiny required for release of transgenic organisms in part on the taxonomic difference between the host organism and the source of the inserted sequence.

A reliable method for eliminating the unwanted ancillary sequences would thus improve commercial viability by increasing public acceptance and simplifying the regulatory process. The prior art has not recognized the importance of this problem, nor has it worked to provide a solution.

Currently, the cost of developing improved crop varieties is extremely high. Thus, it is imperative that commercial cultivars be protected from use by competitive breeders. Current methods of varietal protection require a detailed description of the physical appearance and biochemical attributes of the cultivar which make it unique. However, this type of characterization is subjective and difficult to practice because physiological attributes can easily vary under different growth conditions. Additionally, the use of a protected variety as a parent in a hybrid combination is virtually impossible to detect by description methods because the parental characteristics will be masked in the hybrid. Thus, a reliable method for definitively identifying a proprietary cultivar is required, but lacking in the art.

SUMMARY OF THE INVENTION

This invention relates to methods for producing transgenic plants that contain a gene of interest and that are free of foreign ancillary nucleic acids. These methods allow for the production of plants which thus contain a desired gene, but which are free of vector sequences and/or marker sequences used to transform the plant. The method of transforming such plants calls for transforming the plants with a gene of interest by introduction of the gene on a DNA construct comprising a transposon and foreign ancillary nucleic acids; crossing the transformed plant through self-crossing or with another plant to obtain $F_1$ or more removed generation progeny; and utilizing a means for selecting those progeny that carry the gene of interest and are free of the ancillary nucleic acids. Such progeny may be detected, biochemically, by Southern hybridization, through the use of polymerase chain reaction procedures and other methods available in the art.

The gene of interest may be cloned within the transposon so that upon transposition it is separated from the vector and marker sequences. Crosses are then made to eliminate the vector and marker sequences by selecting progeny in which they do not appear. Alternatively, undesired sequences, such as the marker sequences, may be cloned within the transposon, with the gene of interest on the DNA construct outside of the transposon, so that upon transposition the marker sequences are separated from the gene of interest. Crosses can then be made to eliminate the marker sequences, or undesired DNA, by selecting for appropriate progeny.

Alternatively, methods are also provided for identifying progeny of a plant through creating a molecular fingerprint in the genome of the plant by inserting a DNA fingerprinting construct into the genome, detecting unique sites of insertion of the foreign DNA in the genome, and recording the unique sites of insertion. Then DNA from a second plant suspected of being derived from such a plant is isolated and the presence or absence of the unique sites of insertion are detected. The DNA fingerprinting construct may comprise a transposon element.

Boxes below the line indicate key portions of the plasmid. LB and RB indicate the left and right T-DNA borders respectively. The LIH region is the region of homology required for pMON200 to integrate into the disarmed Ti plasmid pGV3111-SE (Fraley et al. 1985). Ac7 represents the entire Ac element cloned into the polylinker of pMON200. The dotted lines on either side of Ac7 represent maize DNA which flanks the Ac7 element. NPTII is the neomycinphosphotransferase gene which has been engineered to express in plant cells and allows their growth in kanamycin-containing media. This is the selectable marker gene which is undesirable in the final cultivar. SP/SM are bacterial genes encoding streptomycin and spectinomycin resistance and are used to maintain pMON200 in Agrobacterium. NOS is the gene encoding nopaline synthase and is used to confirm transformation events. These various components are further described in Fraley et al. (1985).

Figure 2:
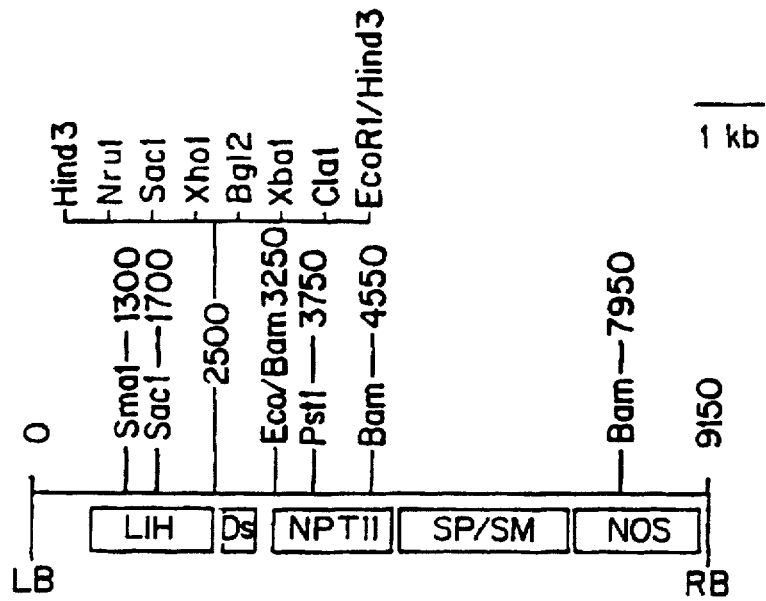

FIG. 2. The plasmid pDs203 is a derivative of pMON200 and contains the 450bp DSI element and flanking maize DNA in the EcoRI site of pMON200. The Ds203 portion is shown as the box with Ds, the dotted lines flanking Ds represent maize DNA.

Figure 3:
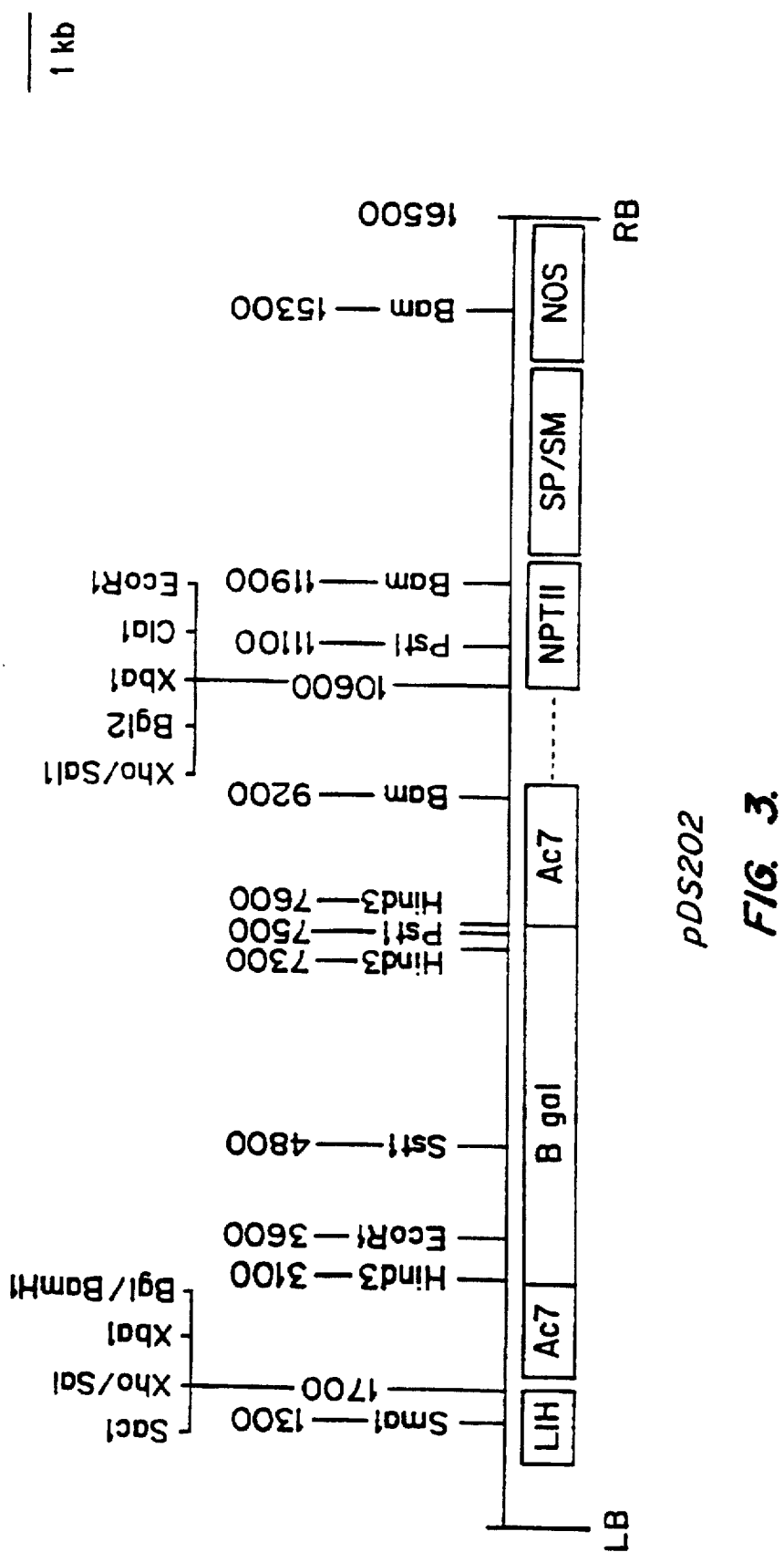

FIG. 3. The plasmid pDs202 was constructed by replacing the central 1.6 kb portion of Ac, bordered by the internal HindIII sites, with the bacterial gene encoding β-galactosidase (Bgal). The remainder of pDs202 is virtually identical to pMAC.

Figure 4:
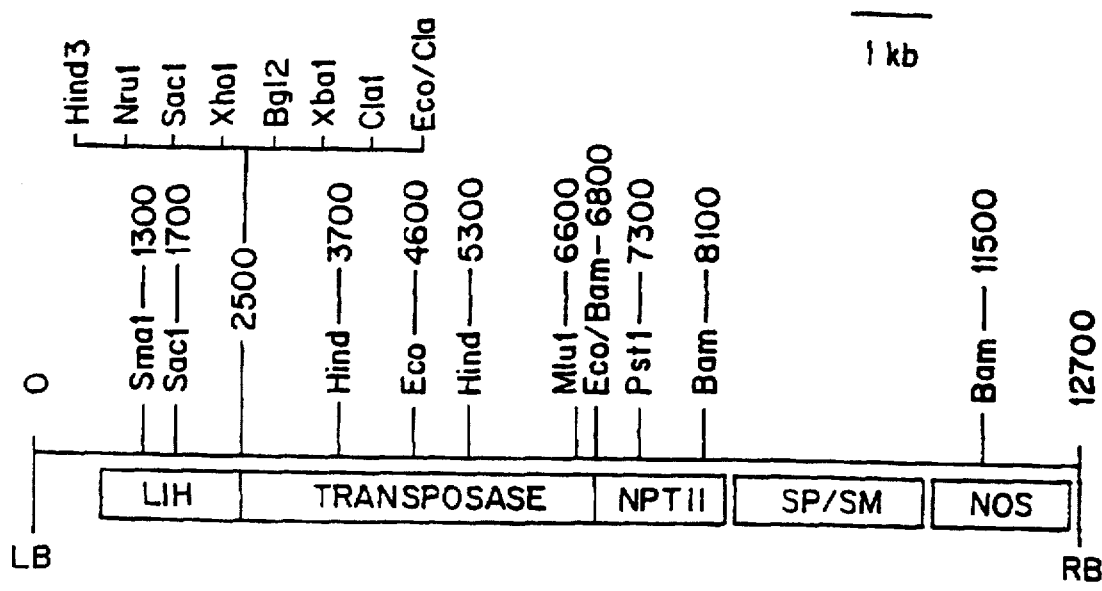

FIG. 4. The vector pTs105 contains the transposase coding region of Ac7 cloned into the polylinker site of pMON200. Both ends of pTs105 have been enzymatically removed to prevent further transposition of this transposase gene.

Figure 5:
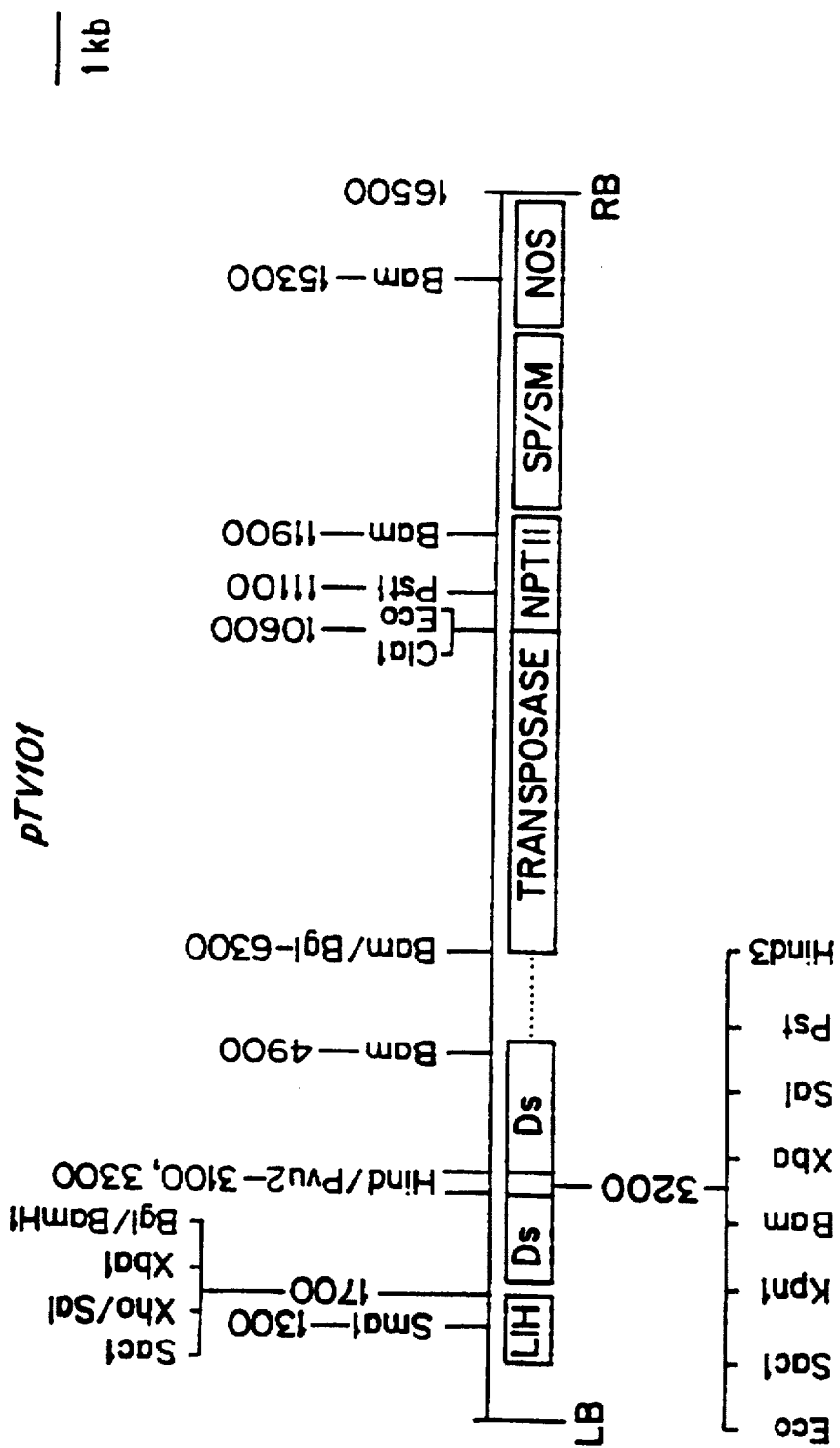

FIG. 5. The plasmid pTV101 contains both the transposase gene and the Ds component on the same pMON200 derivative. In the center of the Ds element, as position 3200, a polylinker site is inserted to allow rapid cloning into this region of pTV101.

Figure 6:
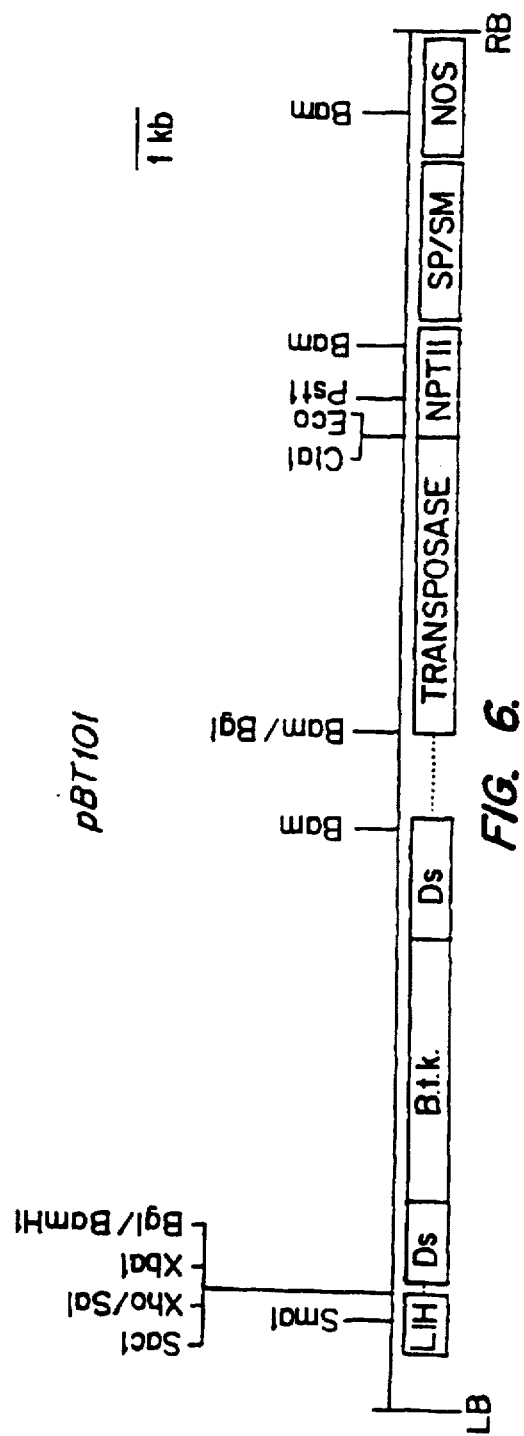
Figure 7:
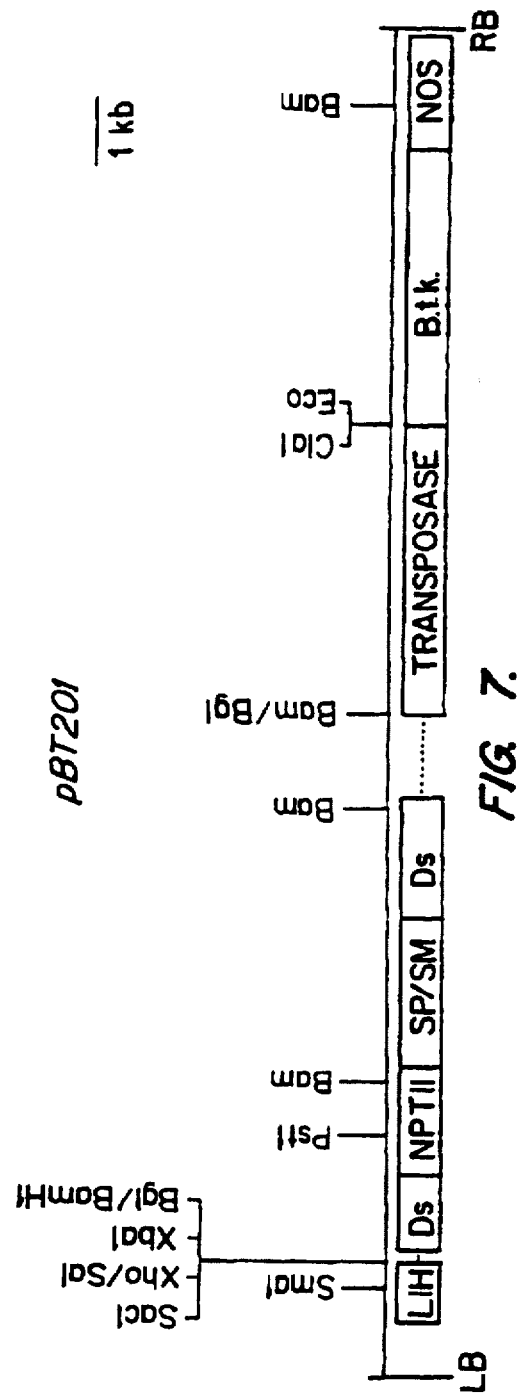
Figure 8:
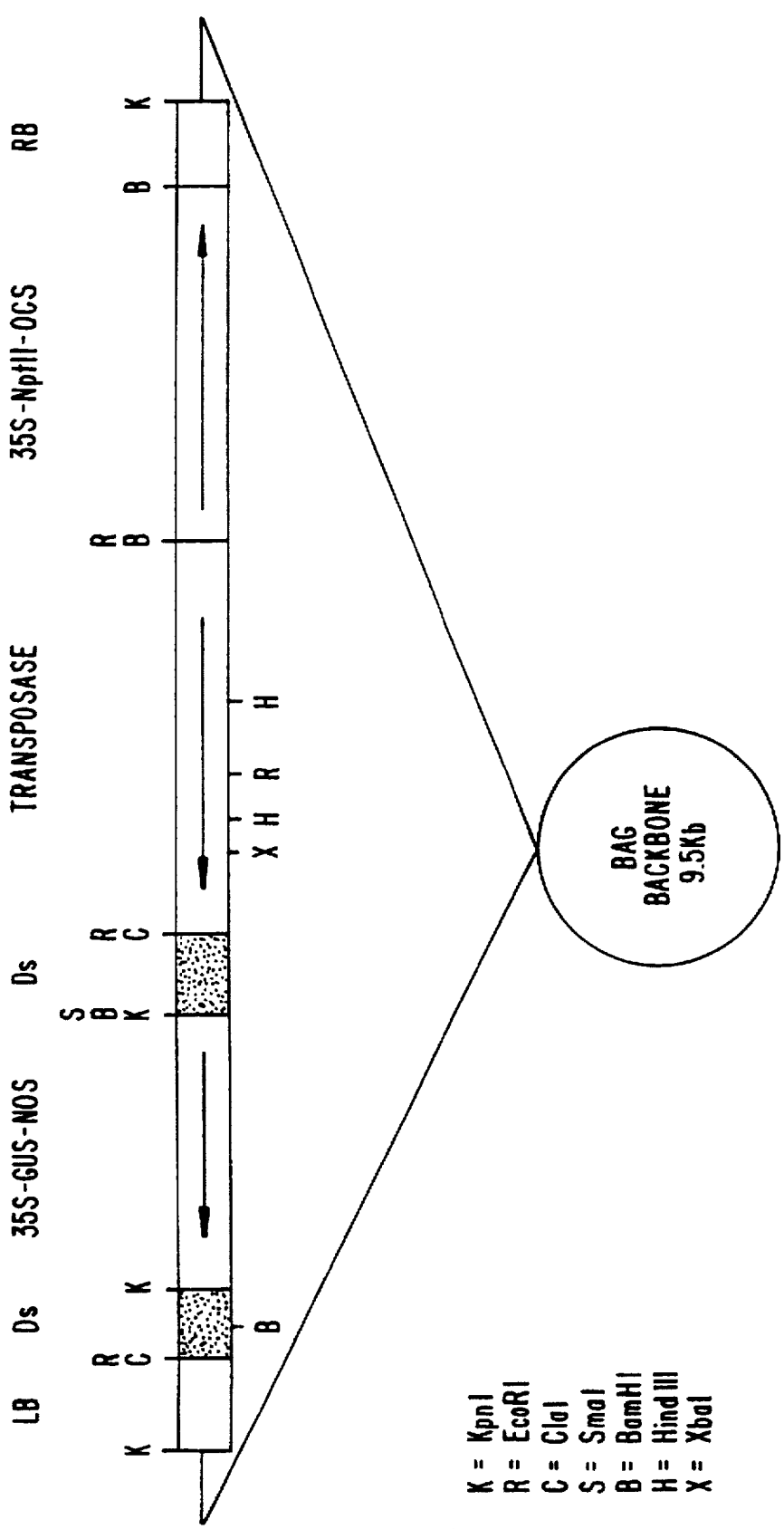
Figure 9:
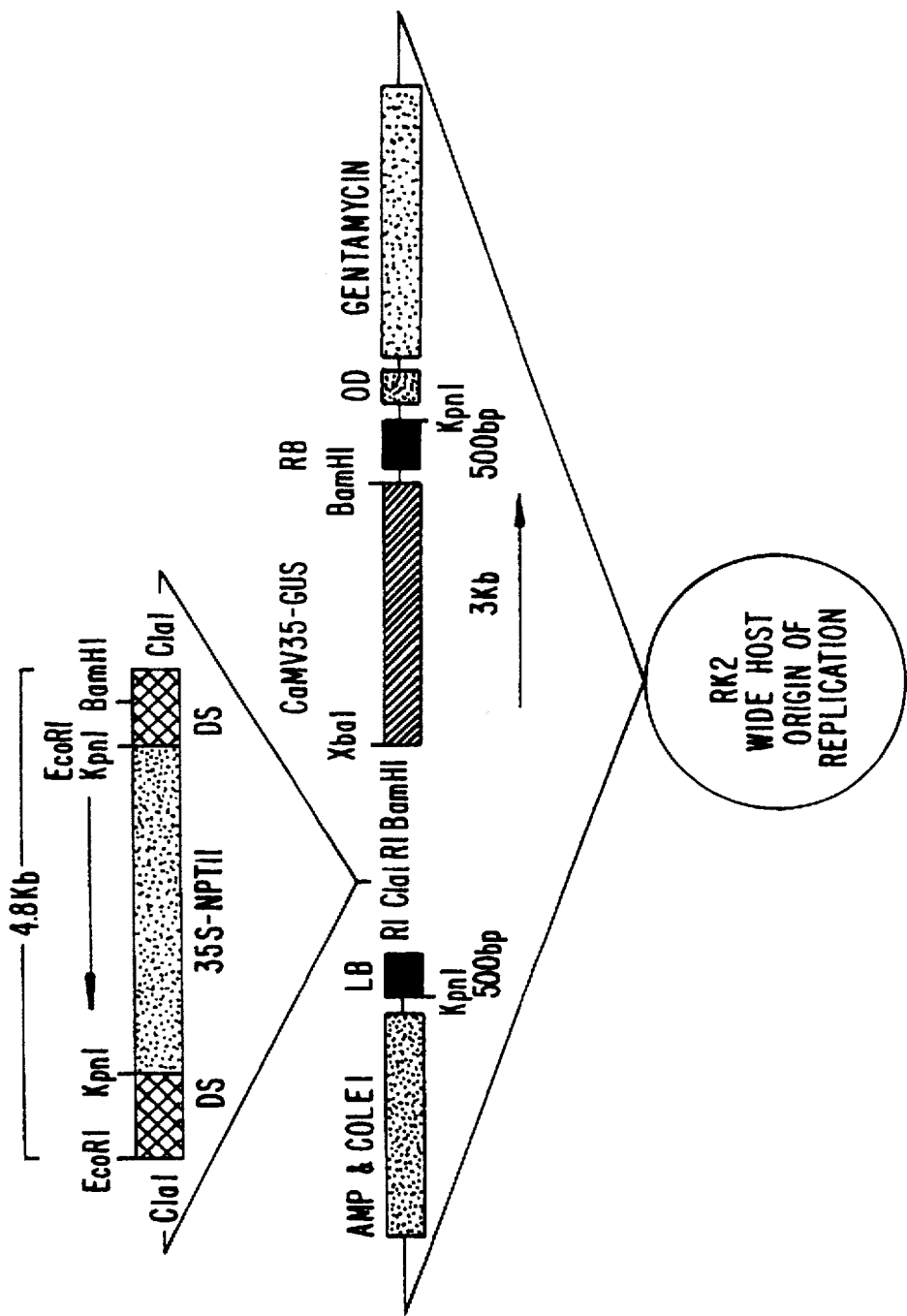

FIG. 6. The plasmid pBT101 would contain the 4 kb insect control protein gene (B.t.k.) isolated from *Bacillus thuringiensis* var. *kurstaki* cloned into the polylinker of pTV101. This plasmid would contain the *B.t.k.* gene flanked by the inverted repeats of Ds as well as the stable transposase encoding gene.

FIG. 7. The plasmid pBT201 illustrates a vector in which the selectable markers NPTII and SP/SM would be placed internal to the inverted repeats of Ds. This conformation would allow removal of the selectable marker genes from the desired transgenic plant without repositioning the *B.t.k.* gene.

FIG. 8. The plasmid pVCY1605 illustrates a vector in which the selectable marker GUS is placed internal to the inverted repeats of Ds.

FIG. 9. The plasmid pVCY1645 illustrates a vector in which the selective marker NPTII is placed interval to the inverted repeats of Ds.

DETAILED DESCRIPTION

This invention provides methods for the removal of undesired nucleic acid sequences, such as vector sequences, from a plant that has been transformed with a desired foreign gene. These methods thus provide transgenic plants that are free of ancillary foreign nucleic acid which typically accompanies the gene of interest during transformation. Reduction of ancillary nucleic acid sequences in the transformed plant would greatly reduce public concern over transgenic plants. Regulatory problems encountered in testing the plants may be reduced and consumer concern over the safety of consumption of the plants should be alleviated.

I. General Methods

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., *Molecular Cloning—A Laboratory Manual*, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

II. Plant Transformation

A. The DNA Construct

For the purposes of this invention a DNA construct is produced which is used in the plant transformation. The "DNA construct" will contain the gene of interest, foreign ancillary nucleic acid sequences and a transposon, all as defined below, such that either the gene of interest or the undesired ancillary sequences will likely transpose with the transposon once transposition occurs.

Alternatively, a "DNA fingerprinting construct" may be used which contains a transposon or other foreign DNA. The random insertion of the DNA into the genome of a targeted plant can be used to create a molecular fingerprint for that plant. The unique insertion site of the DNA will create a restriction fragment length polymorphism that can be used to identify the plant or its progeny. This method is particularly useful in marking proprietary cultivars that otherwise cannot be identified at the molecular level.

The benefits of inserting desired genes into the genome of plants is limitless. A "desired gene" or "gene of interests" is any gene that encodes for a desired property or identifiable phenotype and that is not native to the plant. Preferably, the gene encodes an agronomically useful property or phenotype. Genes of interest, for example, could include genes encoding disease resistance (e.g., viral resistance, fungal resistance, or the gene for the endotoxin of *Bacillus thuringiensis*), genes involved in specific biosynthetic pathways (e.g., genes involved in fruit ripening, oil or pigment biosynthesis, or starch metabolism) or genes involved in environmental tolerance (e.g., salt tolerance, drought tolerance, or tolerance to anaerobic conditions). The nature of the desired gene itself is not critical to this invention. Examples:of such genes and their availability are published and those skilled in the art may also identify and isolate additional desired genes. See, Weising, et al., *Ann. Rev. Gen.* 22:421–478 (1988), incorporated by reference herein.

Transposons of use in this invention refer to sequences of DNA which have the ability to move or to jump to new locations within a genome. Two components are required for transposition: the transposase enzyme which catalyzes transposition and the nucleotide sequences present at the end of the transposon upon which the enzyme acts. Transposons are both autonomous and non-autonomous. Autonomous transposons are those which are capable of both transposing and catalyzing the transposition of non-autonomous elements. Examples of autonomous transposons are the Ac elements and Spm transposons isolated:from maize, all of which have been cloned and well-described in the art. See, for example, U.S. Pat. No. 4,732,856 and Gierl et al., *Plant Mol. Biol.* 13:261–266 (1989) which are incorporated by reference herein.

Autonomous transposons comprise sequences for transposase and sequences which are recognized by the transposase enzyme at the ends of the transposon (the "Ds element"). The sequences for transposase (or the transposase gene) are active independent of the end sequences, i.e., if the end sequences are eliminated, the activity of the transposase gene is preserved and the enzyme encoding element may thus be used in conjunction with a non-autonomous or Ds element to trigger transposition of the Ds element. The transposase gene is evident in the Ts101 and Ts105 elements.

Only the DNA sequences present at the ends of a non-autonomous element are required for it to be transpositionally active in the presence of the transposase gene. These ends are referred to herein as the "transposon ends" or the "Ds element." See, for example, Coupland et al., *PNAS* 86:9385 (1989), incorporated by reference herein, which describes the sequences necessary for transposition. The DNA sequences internal to the transposon ends are non-essential and can be comprised of sequences from virtually any source. This allows one to clone foreign DNA between the transposon ends. If a gene is cloned within the transposon ends, it will transpose with the transposon element. The construct will be stable in the transformed plant until the transposase gene is introduced, either genetically or asexually, into the same plant.

Transposon elements or Ds elements are those non-autonomous elements which can transpose only when a transposase gene is present in the same genome, such as Dissociation (Ds) or Ds1, which have been cloned and well-described in the art. See, for example, Lassner et al., *Mol. Gen. Genet.* 218:25–32 (1989) and Yoder et al. *Mol. Gen. Genet.*, 213:291–296 (1988) both of which are incorporated by reference herein.

Currently, the most preferred transposon system is the Ac/Ds system from corn, though elements from other species may also be used. Many plants, however, are known to contain transposons. They are typically detected by variegation arising from somatic mutation. A review of transposons can be found in Nevers et al., *Adv. in Bot. Res.* 12:103–203 (1987), which is incorporated by reference herein.

Transposons may be isolated from various plant sources by described methods. Transposons are most commonly isolated as an insertion into a gene encoding a well characterized gene product. The steps required for isolating a transposon by this method are: (a) a plant gene responsible for encoding a desirable phenotype is cloned by any of the standard cloning approaches (Sambrook et. al. supra), (b) a transposon-induced mutation at the cloned gene is obtained by screening plants for the inactivation of the cloned gene in populations in which the transposon is known to be active, (c) using the cloned gene as a hybridization probe, the mutant gene obtained from the scored population is obtained, then (d) nucleotide sequence comparisons made between the active gene and the mutant gene are used to identify the transposon insertion.

The prevalence of transposable elements in natural populations has allowed a second method of isolating transposons to be successful. In the process of genetic mapping using restriction fragment length polymorphism (RFLP) mapping, RFLP patterns are occasionally seen which are consistent with an insertion into the scored DNA sequence. This procedure, based on randomly assaying the genome for new insertions, has been successful for identifying transposons.

The DNA construct will also contain foreign ancillary nucleic acids which will also become incorporated into the transformed plant chromosome along with the gene of interest. "Foreign ancillary nucleic acids," "ancillary nucleic acids" or "ancillary sequences" are those nucleic acids that are foreign to the plant being transformed and that are undesired sequences. "Undesired sequences" are those sequences one targets for removal from a transformed plant. If the gene of interest is cloned in the DNA construct within the transposon element, the undesired sequences are those sequences on the DNA construct that are outside of the transposon element, which will be separated from the transposon element upon transposition. If the gene of interest is not cloned in the DNA construct such that it is not within the transposon element, the undesired sequences are the transposon element itself and those sequences that are within the transposon element, which will be separated from the gene of interest upon transposition. A plant that is "free of" foreign ancillary nucleic acids is one in which the undesired sequences are not detectable by standard hybridization procedures, such as by Southern hybridization.

B. Vector Construction

The desired DNA construct will preferably comprise a transposon containing an expression cassette designed for initiating transcription of the gene of interest in plants. Ancillary sequences, of bacterial or viral origin, are also typically included to allow the vector to be cloned in a bacterial or phage host.

The vector will also typically contain an ancillary selectable marker gene by which transformed plant cells can be identified in culture. Usually, the marker gene will encode antibiotic resistance. These markers include resistance to G418, hygromycin, bleomycin, kanamycin, methotrexate, chlorsulfuron, lincomycin, clindamycin, spectinomycin, phosphinotricine, glyphosate and gentamicin. After transforming the plant cells, those cells having the vector will be identified by their ability to grow on a medium containing the particular antibiotic.

Other ancillary DNA sequences encoding additional functions may also be present in the vector, as is known in the art. For instance, in the case of Agrobacterium transformations, T-DNA sequences will also be included for subsequent transfer to plant chromosomes.

A bacterial expression vector may be used if expression of a gene in bacteria is desired. Construction of a bacterial expression vector is typically done by placing the gene downstream from a strong bacterial promoter. Examples of bacterial promoters that might be used include β-lactamase, β-galactosidase, and the phage λpL promoters. The efficiency of translation of mRNA in bacteria is critically dependent on the presence of a ribosome-binding site and its distance from the transcription initiation codon.

For expression in plants, the recombinant expression cassette will typically contain in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5'

(upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Other sequences conferring tissue specificity, response to environmental signals, or maximum efficiency of transcription may also be found in the promoter region. Such sequences are often found within 400 bp of transcription initiation size, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. Herrara-Estrella et al., *Nature*, 303:209–213 (1983). Viral promoters include the 35S and 19S RNA promoters of cauliflower mosaic virus. Odell et al. *Nature*, 313:810–812 (1985). Possible plant promoters include the ribulose-1,3-bisphosphate carboxylase small subunit promoter, the promoter sequence from the E8 gene, and the phaseolin promoter.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434 (1982). Polyadenylation sequences include, but are not limited to, the Agrobacterium octopine synthase signal (Gielen et al., *EMBO J.*, 3:835–846, 1984) or the nopaline synthase signal (Depicker et al., *Mol. and Appl. Genet*, 1:561–573 (1982)).

The use of the transposon in the vector allows the separation of the desired gene from ancillary sequences. Transposons in the DNA construct will be used in two independent configurations. Either (1) the gene of interest will be cloned within the transposon ends into the central, non-essential regions of the transposon or (2) the selectable marker gene sequences used to select the transformed plant will be cloned within the transposon ends into the non-essential regions with the desired gene being cloned outside the transposon. In the first case, mobilization of the transposon will be used to separate the gene of interest from the transforming vector sequences. In the second case, mobilization of the transposon will be used to eliminate the selectable marker sequences from the construct containing the gene of interest.

C. Direct Transformation

The DNA construct described above can be microinjected directly into plant cells by use of micropipettes to mechanically transfer the recombinant DNA. Crossway, *Mol. Gen. Genetics* 202:179–185 (1985). The genetic material may also be transferred into the plant cell using polyethylene glycol, Krens, et al., *Nature* 296:72–74 (1982).

Another method of introduction of nucleic acid segments is high velocity ballistic penetration by small particles with the nucleic acid either within the matrix of small beads or particles, or on the surface, Klein, et al., *Nature* 327:70–73 (1987).

Yet another method of introduction is fusion of protoplasts with other entities, either minicells, cells, lysosomes or other fusible lipid-surfaced bodies, Fraley, et al., *Proc. Natl. Acad. Sci. USA* 79:1859–1863 (1982).

The DNA may also be introduced into the plant cells by electroporation. Fromm et al., *Pro. Natl. Acad. Sci. USA* 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

D. Vectored Transformation

Cauliflower mosaic virus (CaMV) may be used as a vector for introducing the gene of interest into plant cells. (Hohn et al., "*Molecular Biology of Plant Tumors*," Academic Press, New York, pp.549–560 (1982); Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

Another method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science* 237:1176–1183, 1987.

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid. Hoekema, et al., *Nature* 303:179–189, 1983. The transferred DNA region can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, *Nature* 298:85–88 (1981)), promoters, (Lawton et al., *Plant Mol. Biol.* 9:315–324 (1981)) and structural genes for antibiotic resistance as a selection factor (Fraley et al., *Proc. Nat. Acad. Sci.* 80:4803–4807 (1983)).

All plant cells which can be transformed by Agrobacterium and from which whole plants can be regenerated can be transformed according to the present invention to produce transformed intact plants which contain the desired DNA. There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for culturing protoplasts and subsequent plant regeneration from cultured protoplasts.

Method (2) requires (a) that the intact plant tissues, such as cotyledons, can be transformed by Agrobacterium and (b) that the transformed cells or tissues can be induced to regenerate into whole plants.

Most dicot species can be transformed by Agrobacterium. All species which are a natural plant host for Agrobacterium are transformable in vitro. Monocotyledonous plants, and in particular, cereals, are not natural hosts to Agrobacterium. Attempts to transform them using Agrobacterium have been unsuccessful until recently. Hooykas-van Slogteren et al., *Nature* 311:763–764 (1984). There is growing evidence now that certain monocots can be transformed by Agrobacterium. Using novel experimental approaches cereal species such as rye (de la Pena et al., *Nature* 325:274–276 (1987)), corn (Rhodes et al., *Science* 240:204–207 (1988)), and rice (Shimamoto et al., *Nature* 338:274–276 (1989)) may now be transformed.

A preferred Agrobacterium binary vector plasmid (Van den Elzen et al., *Plant Mol. Biol.* 5:149–154 (1985)) will contain a linked drug resistance gene, such as one for kanamycin resistance, to select for transformed plant cells. This transformation vector can be used to generate kanamycin resistant plants for ready screening of transformed plants.

III. Selection and Regeneration of Transformed Plant Cells

After transformation, transformed plant cells or plants comprising the desired gene must be identified. A selectable marker, such as those discussed, supra, is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well. See, e.g., Sambrook, supra.

All plants from which protoplasts can be isolated and cultured to give whole regenerated plants can be transformed. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium; Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browalia, Glycine, Lolium, Zea, Triticum, Sorghum, Malus, Apium, and Datura.

Plant regeneration from cultured protoplasts is described in Evans et al., *Handbook of Plant Cell Cultures*, Vol. 1: (MacMillan Publishing Co. New York (1983)); and Vasil I.R. (ed.), *Cell Culture and Somatic Cell Genetics of Plants*, Acad. Press, Orlando, Vol. I, 1984, and Vol. III (1986).

It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

IV. Separation of the Ancillary Foreign Sequences From the Gene of Interest

Once a plant has been transformed so that the gene of interest, the transposon and ancillary foreign nucleic acids are incorporated into the genome of the plant, the transformed plant is crossed by sexual reproduction in any manner well-known in the art and described for the individual species of plant to obtain an $F_1$ or more removed generation. The crosses ultimately lead to the elimination of the ancillary sequences from the plant. In addition, as will be discussed below, the sequences may be eliminated through somatic segregation.

As discussed above, the constructs, bearing either the gene of interest or the selectable marker gene inserted with the transposon, are introduced into a plant. In the transformed plant, the transposon element of the construction, is stable unless sequences encoding transposase are also introduced into the same plant. Thus, the gene of interest and ancillary sequences will not separate.

Transposase encoding sequences can be introduced into the transformed plant either by asexual transformation with a vector containing transposase sequences or by genetically crossing to a plant which itself contains transposase sequences. The presence of the transposase then allows the transposon to "jump" away from the other inserted DNA.

When transposase sequences are directly transformed into the host plant, they may either coexist on the same plasmid as the Ds element or can be introduced into the plant in a secondary transformation. The transposase gene can also be introduced into the plant bearing the Ds element by sexually crossing two different transgenic plants, one bearing a transposase gene and one bearing the Ds element. In plants bearing both the transposase gene and the Ds element, the transposon element, bearing either the gene of interest or the selectable marker gene, will transpose to a new chromosomal location, distinct from the location of the transforming DNA construction. While transpositions sometimes go to genetically linked sites, transposition to more distant regions of the genome are also frequently recovered.

After the transposon has moved to a new locus, the next step is to cross the plant to eliminate the ancillary sequences. This is typically done using sexual crosses. The crossings may be self-crossings, back crossings or crossings with any other plant which is compatible for sexual reproduction with the objective of obtaining progeny that carry the gene of interest and which are free of the ancillary nucleic acids. Such crossings would be typical of a commercial breeding program.

As discussed above, sexual crossings result in the independent assortment of unlinked genes in progeny populations. When the Ds element has transposed to a position unlinked to the initial transferring vector each sequence will independently assort in the progeny. Therefore, some of the progeny obtained from the crossings will contain the gene of interest within the transposon ends without the ancillary sequences if the gene was cloned in the transposon. Alternatively, the gene of interest may be at its original location from which the selectable marker gene has been removed by a transposition event if the marker was cloned in the transposon ends.

$F_1$ generation here refers to the progeny of the cross between the transformed plant and its mate and to the progeny resulting from self-crossing. "More removed generation progeny" refers to those progeny which result from subsequent crosses that descend from the transformed plant so long as one of the members in the cross contains the gene of interest.

This procedure is also compatible for producing transgenics with asexually propagated crop species. Transposition can also occur during mitosis and the transposon can insert onto a chromatid, leaving the sister chromatid unaltered. In these cases, somatic segregation will eliminate the ancillary sequences from the cells or whole plants bearing the gene of interest. One can detect the presence of somatically segregated cells in the transformed plant or more removed generation that carry the gene of interest and are free of the ancillary nucleic acids. A plant may then be regenerated from such cells.

V. Identification of Progeny Free of the Ancillary Sequences

Means for selecting those progeny that carry the gene of interest and are free of the ancillary nucleic acids include those methods available which allow one to identify the presence or absence of certain known nucleic acid sequences. The detection of the ancillary foreign nucleic acids can be determined by a variety of standard nucleic acid hybridization techniques which are sufficiently sensitive to assure that no microbial genetic material remains in the host plants. Such techniques would encompass homogeneous hybridization reactions where both complementary nucleic acids are free in solution and heterogeneous assays where one nucleic acid is bound to a solid support such as a slot blot or a Southern blot assay. The specific hybridization technique is not critical. A number of methods are generally described in *Nucleic Acid Hybridization, A Practical Approach*, (Hames, B. D. and Higgins, S. J., Eds.) IRL Press (1985) which is hereby incorporated herein by reference.

It is preferred that the sensitivity of the assay be enhanced through use of a nucleic acid amplification system. Such systems multiply the absolute numbers of the target nucleic acid being detected. The specific amplification system is not critical to this invention and there are at least two systems available for use.

The first system is the polymerase chain reaction (PCR) system. This amplification procedure is a template dependent DNA polymerase primer extension method of replicating select sequences of DNA. The method relies upon the use of an excess of specific primers to initiate DNA polymerase replication of specific sequences of a DNA polynucleotide followed by repeated denaturation and polymerase extension steps. The PCR system is well known in the art (see U.S. Pat. Nos. 4,683,195 and 4,683,202, which are incorporated by reference herein). Reagents and hardware for conducting PCR are available commercially through Perkin-Elmer/Cetus Instruments (PECI) of Norwalk, Conn.

The second amplification system is the ligase amplification reaction (LAR). LAR, like PCR, uses multiple cycles of alternating temperature to amplify the numbers of a targeted sequence of DNA. Unlike PCR, LAR does not use individual nucleotides for template extension. LAR relies instead upon an excess of oligonucleotides which are complementary to both strands of the target region. Following the denaturation of a double stranded template DNA, the LAR procedure begins with the ligation of two oligonucleotide primers complementary to adjacent regions on one of the target strands. Oligonucleotides complementary to either strand can be joined. After ligation and a second denaturation step, the original template strands and the two newly joined products serve as templates for additional ligation to provide an exponential amplification of the targeted sequences. This method has been detailed in *Genomics* 4:560–569 (1989) which is incorporated herein by reference.

The detection and amplification systems described here are routinely practiced by those of skill in the relevant art. This invention is not limited to any particular detection or amplification system. As other systems are developed, they may also find use in this invention. For example Southern hybridization methods may be used by digesting the subject nucleic acids with restriction enzymes and probing the blots prepared from the digests with probes for the sequences of interest or probes which otherwise indicate the presence or absence of the sequence of interest. Examples of this method may be found in Yoder et al., *Mol. Gen. Genet.* 213:291–296 (1988), which is incorporated by reference herein.

In addition, chemical markers can be used to identify whether a sequence is present or not if the marker is expressed by a phenotype readily observable. For instance, nondestructive assays for kanamycin sensitivity are available. Thus, transformed plants that bear the gene of interest but have lost the kanamycin resistance gene can be easily identified. See, Weide, et al., *Theor. Appl. Genet.*, 78:169–172 (1989), which is incorporated herein by reference.

VI. Molecular Fingerprinting

The present invention also includes the use of introduced foreign DNA as a genetic marker in crop species to be used in varietal protection. The introduced foreign DNA can be any sequence that is distinguishable from the naturally occurring sequences in the plant. The DNA is preferably distinguished using standard techniques in the art such as Southern hybridizations.

Virtually any foreign DNA can be used. For the reasons discussed in the background section above, the DNA is preferably of plant origin. Preferred plant sequences include maize transposons, such as the Ds element. In that case, the Ds element and a transposase gene are introduced into the same plant by any of the different gene transfer technologies discussed above. The Ds element transposes to a new unique chromosomal location because of the presence of the enzyme. The plant is grown to maturity and either self-pollinated or outcrossed and progeny collected. By DNA analysis techniques such as those described above, a progeny plant is identified which contains a transposed Ds element, but does not contain the transposase gene. Typically, DNA isolated from the progeny is digested with a number of different restriction enzymes, electrophoresed, blotted onto a membrane by the Southern procedure, and probed with a labeled Ds sequence. The restriction pattern obtained will be unique for each transposition event because of the randomness of the insertion. Thus, a restriction fragment length polymorphism (RFLP) is created in the cultivar.

RFLPs have been extensively used for accurate and systematic mapping of loci associated with quantitative traits. See, e.g., Botstein, et al., *Am. J. Hum. Genet.*, 32:314–331 (1980) which is incorporated herein by reference. The technology, however, requires that a detectable difference be present in the individual of interest. The method presented provides a method for creating a detectable difference. RFLP technology can then be used as a means of fingerprinting the genome of that plant and its progeny.

Many species do not have the genetic variability to allow cultivar differentiation. In vegetatively propagated crops, for instance, different cultivars arising as bud sports will be virtually identical genetically. By introducing an RFLP genetic marker, lines that are similar in most respects can be readily distinguished. A number of features of this invention make it valuable for use in different crop plants. Since the insertion site is unique for each different transformation event, it is easy to make markers in different cultivars using the same procedure. Since the insertion site is random, it would be virtually impossible to duplicate the insertion event in other cultivars. There are a large number of restriction enzymes which can be used in the diagnosis so the cultivar can be unambiguously marked.

The transposed Ds is a preferred dominant marker and therefore can be detected in hybrid lines containing multiple parentage. This makes it possible to determine if the protected line was used as a parent. The element is stable in the absence of transposase, therefore the "fingerprint" can be used throughout the use of the cultivar. Ds is a naturally occurring sequence present in all existing lines of corn. Since it encodes no protein and has no genetic effects in the absence of transposase, there should be few regulatory concerns. The system is versatile in that it can be used to mark a finished cultivar or can be introduced at early stages of a breeding program. Since transformation procedures are rapidly becoming available for a number of crop plants, it is possible to use the identical system for the protection of a number of different species.

In practice, once a breeder has identified a promising line which warrants commercialization, a foreign sequence is introduced into a plant of that variety. At least three different ways can be used to introduce the DNA into the plant. The transformation vector can contain both a transposase gene and the Ds marker. The elements can be introduced onto the same plant by co-transformation of two different vectors, or the sequences can be introduced into two different plants and combined by genetic hybridization. The transgenic lines would be grown and either selfed or crossed to a non-transformed sibling, depending on the reproductive nature of the species as well as the stage of the breeding program. In progeny which contained a Ds element but no transposase gene, the Ds insertion site would be characterized as described above. Once such an insertion site fingerprint had been identified, it would be recorded for future use.

Any future varieties that the breeder suspected were derived from proprietary material could be simply examined for the presence of the unique Ds insertion. DNA from the suspect lines would be digested with the same battery of enzymes used to characterize the site in the protected cultivar and probed with the Ds element. Reproduction of the insertion pattern as obtained from the parent would indicate common heritage.

A number of modifications to this method of varietal protection can be envisioned using transposons. It is possible to make transformation vectors which have the transposase gene and the Ds marker on the same plasmid, hence simplifying the introduction process. The Ds element could be constructed such that its diagnosis could be simplified; such alterations would include cloning easily assayed genes into the element or other sequences allowing for non-radioactive detection. It is also possible to use multiple Ds insertions to mark more than one chromosome per plant.

VII. Optimizing Gene Expression

Variation in gene expression is observed based on the location of the gene in the chromosome. Jones et al, EMBO 4:2411–2418 (1985). The methods of this invention may be used to optimize expression of the gene of interest. Transposition of the gene of interest may be triggered, as described above, by inserting the desired gene within the transposon ends, to obtain transgenic plants that have the desired gene and that have desired expression levels. A transformed plant is obtained which carries the desired gene cloned within the transposon ends. Transposition is triggered by any of the methods described above and resulting progeny or transformants are selected which have optimal gene expression. This method may be particularly advantageous for those plants that are difficult to transform. Once a transformed plant is obtained that contains the gene of interest within a transposon, transposition is induced by crossing or somatic segregation until a plant with optimal gene expression is obtained. The resulting progeny are examined so that those with optimal gene expression are selected. Optimal gene expression is a subjective determination based on the gene of interest and the phenotype it encodes.

VIII. Additional Definitions

For the purposes of this invention a "plant" will include a plant cell, a plant seed and any part of a plant. A "transgenic plant" is any plant which has incorporated in its genome foreign nucleic acid.

The following examples are provided for illustration and are not to be construed as a limitation upon the claims.

EXAMPLES

I. Vector Construction

Figure 1:
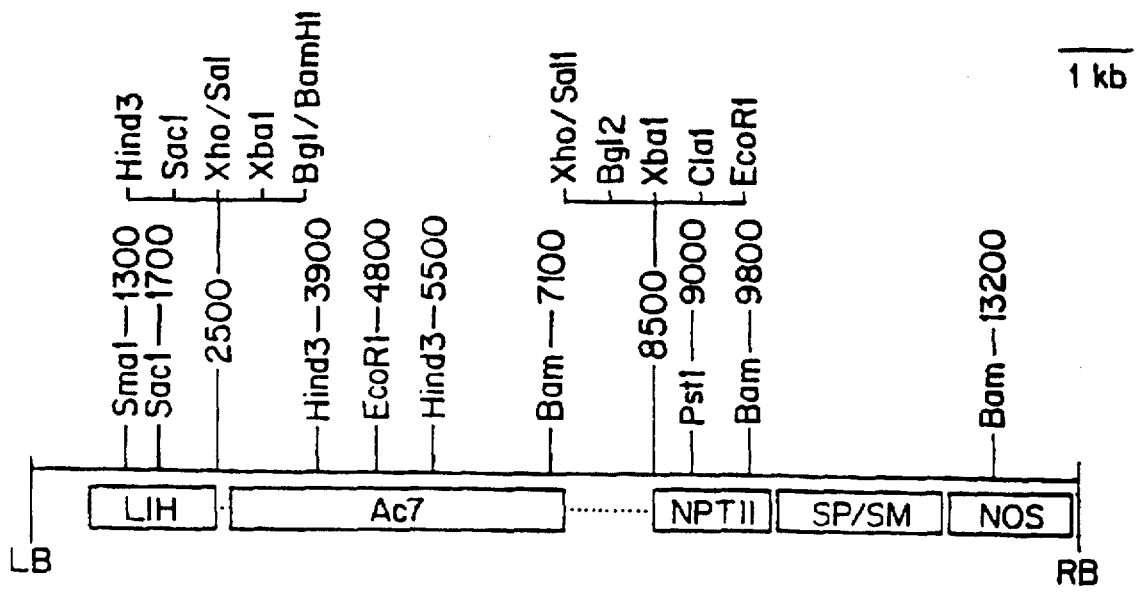
FIG. 1. The structure of the Ac containing plasmid pMAC is diagrammed. The plasmid was derived from pMON200 (Fraley et al. *Biotech.* 3:629–635, 1985) by cloning a Sal I-Pst 1 restriction fragment containing Ac7 (Behrens et al. *Mol. Gen. Genet.* 194:346–347, 1984) into the Xho site of pMON200. A few key restriction enzyme recognition sites and their map positions are shown. The orientation of the map illustrates the plasmid following insertion into the plant genome.

A. Plasmids Incorporating Ac and Ds Elements with a Gene of Interest on Separate Vectors 1. Construction of pPMAC A lambda clone containing the Ac7 element and flanking wx sequences (Behrens et al. *Mol. Gen. Gent.* 194: 346–347, 1984, incorporated by reference herein) was digested with BglII and subcloned into the BamHI site of pUC13 (Messing, J., *Methods in Enzymology*, 101 (1983)). This intermediate vector was digested with SalI and PstI, and the 6 kb fragment containing Ac was cloned into the XhoI site of the Ti-based vector pMON200 (Fraley et al. *Biotech* 3:629–635, 1985, incorporated by reference herein). The resulting construction was called pMAC. A restriction map of the transforming portion of pMAC is shown in FIG. 1.

2. Construction of pDs203

The vector pDs203 is a derivative of pMON200 that contains the Ds1 element together with flanking maize Adh1 sequences (Sutton et al. *Science* 223: 1265–1268, 1984, incorporated by reference herein). It was prepared by blunt-end cloning of the 750 bp HindIII-BamHI fragment of pDs2.A (Sutton et al., *Science* 223:1265 (1984)) into the EcoRI site of pMON200. A map of this construction is shown in FIG. 2.

3. Construction of pDs202

Plasmid pDs202, a derivative of pMAC, contains a bacterial β-galactosidase gene (Bgal) replacing the central HindIII fragment of Ac. It was constructed in two steps. An 800 bp SacI fragment of T-DNA which harbored a HindIII site was deleted from pMAC by digesting pMAC with SacI and recircularizing the derivative plasmid. After digestion with HindIII, which excises a 1.6 kb fragment from the center of the Ac element, the pMAC derivative was ligated with a 4.7 kb HindIII fragment containing an *E. coli* β-galactosidase gene under the control of a *Bacillus subtilis* polC promoter (Ott et al. *Mol. Gen. Genet.* 207: 335–341, 1987). The ligation mixture was transformed into *E. coli* DH5α, and the recombinant plasmid was selected by screening for spectinomycin and streptomycin resistant blue colonies on X-gal (5-bromo-4-chloro-3-indolyl β-D-galactopyranoside) plates. The Ds element, designated Ds202, is diagrammed in FIG. 3.

4. Construction of Tranposase Element Ts105

To construct a stable transposase element, the end of Ac nearest the 3' terminus of the Ac transcript was deleted. pJAC was digested with ClaI, which cleaved a single site in the pBR322 vector. Exonuclease III and S1 nuclease were used to generate plasmid deletion derivatives as described by Henikoff (1984), except that ClaI linkers were ligated to the blunt ends before recircularization and transformation into *E. coli*. DNA isolated from the colonies was assayed by restriction analysis to find a derivative with about 50 bp deleted from the end of Ac. A 4.3 kb fragment containing the entire Ac transposase coding region was obtained by digestion with Cla and Bam HI. The ends of the BamI-ClaI fragment containing the transposase gene were filled-in with Klenow enzyme and deoxynucleotide triphosphates and the fragment was cloned into EcoRI digested, blunt-ended, and dephosphorylated pMON200. The element, designated Ts105, is diagrammed in FIG. 4.

5. Construction of DTV101

DNA from pDs202 is digested with Hind III, and the overhanging ends are filled in using Klenow polymerase and deoxynucleotides. In a separate reaction, the plasmid pUC19 (Yanische-Perron, C. et al. *Gene* 33:103–119 (1985) is digested with PvuII and the 30 base pair fragment containing the polylinker is isolated on a preparative agarose gel. The ends of this fragment are similarly filled in with the Klenow polymerase and this 300 bp fragment is inserted into the blunt-ended HindIII site of pDs202. Following confirmation of this intermediate vector, the vector is digested with Bgl2 and ClaI resulting in linearization of the vector with incompatible Bgl2 and ClaI termini. In a separate reaction, the 4.3 kb transposase encoding fragment from pJAC is isolated following digestion with BamH and ClaI as described above. This fragment is ligated into the Bgl2, ClaI digested pDs202 intermediate. This vector, pTV101, contains a non-autonomous Ds element with a polylinker in its internal portion as well as a stable transposase encoding sequence, and is diagrammed in FIG. 5.

6. For Construction of pBT101 and pBT201 Containing the *B.t.k.* Gene, see Section III Below II. Transformation and Analysis of Transgenic Plants A. Plant Transformation The above constructions were introduced into *A. tumefaciens* GV311SE (Monsanto, St. Louis, Mo.) by triparental mating as described by Fraley et al. (1985). The *Lycopersicon esculentum* x *L. pennelli* F$_1$ hybrid and *L. esculentum* cultivars VF36 and VFNT Cherry were transformed by an adaptation of published transformation procedures (Koornneef et al. *Plant Sci*. 45:201–208, 1986; Fillatti et al. *Bio/Technology* 5:726–730, 1987). Seeds were surface sterilized for one hour in 50% commercial bleach and germinated in MSSV medium (Fillatti et al. 1987). Four- to seven-day-old cotyledons were excised and placed into freshly prepared tobacco feeder plates, prepared by decanting 1–2 mls of tobacco cells in suspension culture onto 2Z medium (Thomas and Pratt *Theor. Appl. Genet*. 59:215–219, 1981). After 48 hours the cotyledons were immersed for 5 min in an overnight culture of Agrobacterium diluted to an OD$_{600}$ of 0.1. They were then blotted dry and replaced on to the feeder plates. After 24 hours the explants were placed into 2 Z medium supplemented with 350 mg/l carbenicillin (Pfizer, New York, N.Y. and 100 mg/l kanamycin sulfate (Boehringer-Mannheim, West Germany). Excised shoots were rooted in medium containing 50 mg/l kanamycin. In order to ensure that each transformant was derived independently, only one kanamycin resistant seedling was propagated per explant.

The transgenic plants were analyzed using Southern blot analysis. Genomic DNA was isolated from frozen plant tissue by the CTAB method described by Bernatzky and Tanksley *Theor. Appl. Genet.* 72:314–321 (1986) incorporated by reference herein. Ten micrograms of genomic DNA were digested with restriction enzymes according to manufacturers' recommendations with the addition of 4 mM spermidine (Sigma Chemical Co., St. Louis, Mo.). The samples were separated electrophoretically in 0.8% agarose gels and transferred to Zeta-probe (BioRad Laboratories, Richmond, Calif.) or Hybond-N (Amersham, Arlington Heights, Ill.). Prehybridization (4h) and hybridization (16h) were conducted at 42° C. in 5xSSC, 10xDenhardt's solution (Denhardt, *Biohem. Biophys. Res. Commun.* 23:641 (1966)), 50 mM sodium phosphate buffer (pH 7.0), 10% dextran sulfate, 1% SDS, 500µg/ml denatured salmon sperm DNA (Sigma), and 50% formamide. After hybridization, the filters were washed for 2 h at 65° C. in 0.2xSSC, 1% SDS, and 0.1% sodium pyrophosphate; the washing solution was changed 4 or 5 times. Before reprobing, filters were stripped with two 15 min washes at 95° C. using the wash solution.

A 4.3 kb ClaI-BamHI fragment from pJAC-D (Yoder et al. 1988) was used as the Ac specific probe. DNA for the wx specific probe was isolated as a 3.2 kb SalI fragment from pSALC (Shure et al., *Cell*, 35:235–242 (1983)). A 0.75 kb fragment homologous to Ds1 and flanking maize Adh1 sequences was isolated from pDS2.A (Sutton et al. *Science* 223:1265–1268 , 1984) by digestion with HindIII and BamHI. A 300 bp DNA fragment used for the internal Ds1 probe was synthesized using the polymerase chain reaction (Saiki et al. *Science* 239:487–491, 1988) on 1 µg of pDS2.A (Sutton et al. 1984) with the primers CGCTCCTCACAG-GCTCATCTC (SEQ ID No.: 1) and CCTCCGCAAATCT-TCGAACAG. (SEQ ID NO.: 2) The DNA was amplified for 30 cycles using the following regime: (1) 2 min at 96° C.; (2) 2 min at 45° C.; and (3) 2 min at 72° C. All the DNA fragments used for probes were electrophoresed twice through agarose gels, the second separation being done in low melting point agarose. The agarose concentration was diluted to 0.5% or less with H$_2$O, and the DNA was labelled by the random primer method (Feinberg and Vogelstein *Anal. Biochem.* 132:6–13, 1983) using a commercial kit (Amersham).

B. Analysis of Transformed Plant Cells

1. Ds1 Excised in Response to Ac

DNA from two primary tomato transformants containing Ds1 was examined by Southern analysis to determine the integrity and number of T-DNA insertions. Southern analysis of plant T27-03 indicated the presence of one T-DNA left border and one right border, suggesting that the plant contained a single copy of the Ds1 element. Analysis of the second plant indicated that transformant T26-18 contained two left borders and two right borders and suggested the presence of two copies of the Ds1 element which were not linked in tandem T-DNA insertions. The analysis of DNA isolated from plant T16-03, using a strategy described in Yoder et al. *Mol. Gen. Genet.* 213:291–296, (1988) incorporated by reference herein indicated the presence of at least one active Ac element.

Plants transformed with Ds1 were used as pollen donors in crosses to the Ac transformants. F$_1$ progeny were grown and DNA was isolated from leaf tissue of individual progeny. Because the parents were hemizygous for the introduced genes, we expected the transposable elements to be transmitted to approximately 50% of the progeny of plants T16-03 and T27-03 and approximately 75% of the progeny of plant T26-18. We performed Southern analysis to determine which progeny inherited Ac, Ds1 or both. In addition, it was possible to determine whether Ds1 excised from its original location.

The resident location of a transposable element, as described here, refers to its original location on the T-DNA. When an element excises during transposition, an empty donor site consisting of the T-DNA without the element remains. After digestion of plant DNA with BamHI and HindIII, the Ds1 resident location is on a 2.1 kb restriction fragment; if Ds1 excises from its resident location, an empty donor site of 1.7 kb is predicted (FIG. 1). A BamHI-HindIII double digestion of Ac yields three restriction fragments homologous to the Ac probe used in these analyses. Two 1.6 kb restriction fragments are internal to Ac, and therefore are present regardless of the location of Ac in the tomato genome. When Ac is at its resident location in the T-DNA, the size of the third restriction fragment is 2.4 kb. If Ac transposes, this third restriction fragment consists of 1.2 kb of Ac and flanking tomato DNA extending to the nearest BamHI or HindIII site; thus this restriction fragment is of a different size for each location of Ac in the tomato genome. The variation of banding patterns (Ac probe) suggests that Ac is at locations distinct from its resident location in all the progeny shown.

Southern hybridization analysis of 24 F$_1$ progeny resulting from the cross between Ac (T16-03) and Ds1 (T27-03 and T26-18) is shown in Table 1. The segregation of Ac and Ds shown in Table 1 is consistent with the presence of one Ds1 locus in T27-3, two unlinked Ds1 loci in T26-18, and a single Ac locus in T16-3. Five progeny contained Ds1 but no Ac; no empty donor site was detected in those plants. Eleven siblings contained both Ac and Ds1; all had a band of the size predicted for an empty donor site. The ratio of resident site to empty donor site varied from plant to plant as would be expected if the material examined contained both transposed and nontransposed Ds1 elements. These results show that Ds1 is stable in the absence of Ac. However, when an Ac element is present in the same plant, Ds1 can excise.

TABLE 1

Segregation of Ac, Ts, and Ds in F$_1$ progeny

| Cross[a] | Total | Ac/Ds[b] | Ac/—[b] | —/Ds | — |
|---|---|---|---|---|---|
| T16-03 × T27-03 | 16 | 6 | 3 | 2 | 5 |
| T16-03 × T26-18 | 9 | 6 | 0 | 3 | 0 |
| T16-12 × T27-03 | 14 | 3 | 3 | 3 | 6 |
| T16-03 × T20-14 | 14 | 2 | 3 | 6 | 3 |
| T16-12 × T20-14 | 5 | 3 | 2 | 0 | 0 |
| T16-03 × 88-119 | 20 | 8 | 4 | 5 | 3 |

[a]The female parent is shown first and the male parent follows. T16-03 contained Ac, T26-18 and T27-03 contained Ds1, T16-12 contained Ts101, T20-14 contained Ds202, and 88-119 contained Ds204.
[b]Ac refers to plants containing Ac or Ts101.

2. A Stable Ts Element Activated Ds1

Three primary transformants containing Ts101 were analyzed by Southern hybridization. A BamHI-HindIII double digest of Ts101 yielded three restriction fragments homologous to the Ac probe; two 1.6 kb fragments were internal to the element and one 1.1 kb fragment extended into the T-DNA. If Ts101 transposed to new locations in the tomato genome, the 1.1 kb fragment would be a different size depending on the location of the nearest HindIII or BamHI site in the flanking tomato DNA. We detected only the 1.6 kb and 1.1 kb bands when we analyzed the three primary transformants.

A transgenic plant containing Ds1 (T27-03) was crossed to a transgenic plant containing Ts101 (T16-12), and the F$_1$ progeny were examined by Southern analysis. The segregation of Ts101 and Ds1 are shown in Table 1, and are consistent with the presence of a single locus of Ts101 in T16-12. When probed with an Ac probe, none of the progeny exhibited any bands besides the 1.6 kb and 1.1 kb fragments. When probed with a fragment containing both Ds1 and Adh1 sequences, the empty donor site was found in the three plants which contained both the Ts and Ds elements; the three siblings which contained only Ds had no empty donor site. Ds1 was stable in the absence of Ts101, but excised from its resident location in all plants containing Ts101.

Thus, the Ds elements, Ds202 and Ds1, are stable in transgenic tomato plants in the absence of an introduced transposase. They can be transactivated in transgenic tomato plants by crossing with transgenic plants containing an active transposase. The Ds elements both excise from their resident locations in the T-DNA and reintegrate at new locations in the tomato genome.

In addition to using a natural Ac element to activate Ds elements, we used a stable derivative, Ts101. Since Ts101 catalyzes transposition of Ds elements, the 50 bp at the 3' end of Ac are not necessary for the transacting function of Ac. This finding is consistent with predictions based on the Ac transcript mapping of other workers which suggests that the Ac transcript ends 265 bp from the Ac terminus.

We examined three primary transformants and six progeny which contained Ts101. Since none of the plants contained any fragments besides the 1.6 kb and 1.1 kb bands diagnostic of Ts101 at its resident location, we did not detect transposition of the element.

3. Ds1 Reinserted in the Tomato Genome

The Ds probe contained both Ds1 and flanking Adh1 sequences. We expected that plants containing an empty donor site would also contain new bands resulting from Ds integrated at new locations in the tomato genome. No such bands were detected even under conditions that could allow the detection of a band present in less than one-tenth of the plant cells. $F_1$ plant (88-207B) containing both Ac and Ds1 was self-pollinated. The $F_2$ progeny were assayed for the presence of new Ds1 containing bands. Since $F_2$ zygotes are formed by the union of single cells of the male and female gametophytes, any transposed Ds1 elements transmitted to the zygote must be present in either one or two copies per cell, an abundance we can easily detect by Southern analysis. The progeny of plant 88-207B segregated for the presence of Ds1 at several new locations. Therefore, Ds1 reintegrated at new locations in the tomato genome. Our inability to detect these new locations in the $F_1$ was most likely due to the low frequency of any particular location in the plant tissue sampled.

4. Ds202 Was Activated by Both Ac and TS101

Since Ds202 is a derivative of Ac which contains a bacterial β-galactosidase gene replacing the central 1.6 kb HindIII fragment of Ac, the analysis of plants containing both elements is complicated by their sequence similarity. However, the resident and empty donor sites of Ac and Ds202 can be distinguished using EcoRI-SmaI double digests. Using the wx probe, which is homologous to sequences flanking both Ac and Ds202, the resident band for Ac is 4.3 kb, and the empty donor site is 2.6 kb. Using the same probe, Ds202 has a 3.5 kb resident band and an empty donor site of 1.8 kb.

Tomato plants containing Ds202 were crossed to plants containing Ac and TS101. The segregation of Ds202 in the progeny was consistent with a single locus having been introduced in the transformation of plant T20-14 (Table 1). In the analysis of progeny segregating for Ac and Ds202, the two lanes which contained both Ac and Ds202 are the only lanes which exhibited the empty donor site of the Ds202 element. The three $F_1$ progeny which contained Ts101 and Ds202 are the only lanes which exhibited the empty donor site of the Ds202 element. The three $F_1$ progeny which contained Ts101 and Ds202 all contained an empty donor site. Two siblings which contained only Ds202 and not Ts101 did not contain an empty donor site. Ds202 was stable in plants lacking an introduced transposase, and excised from its resident location in all the plants examined which contained either Ac or Ts101.

When DNA isolated from plants containing Ds202 is digested with XbaI, a β-galactosidase probe hybridizes to a 6.7 kb fragment when the Ds element is at its resident location; if Ds202 transposes it is predicted to be on a different size fragment, larger than 6.5 kb. To determine if Ds202 integrated at new locations in the tomato genome, we subjected the $F_1$ plants (progeny of Ac×Ds202 and Ts101× Ds202 ) to such an analysis; we only detected the 6.7 kb band indicative of Ds202 at its resident location. We subsequently analyzed $F_2$ progeny of an Ac×Ds202 cross. The Ds202 transformant used to generate the $F_1$ parent, T22-25, contained multiple T-DNA insertions, and multiple loci of Ds202. When 20 $F_2$ plants were examined, 6 contained the resident band and a new 8.8 kb band suggesting that one copy of Ds202 had transposed to a new location in the $F_1$ parent.

C. Characterization of the Sexual Transmission of Transposed Ac Elements from the $R_0$ to the $F_1$ Generation of Transgenic Tomato Plants Tomato cultivar VF36 was transformed with pMAC as described above. The primary transformants are called the $R_0$; progeny which result from selfing $R_0$ plants are $F_1$ for the purposes herein.

Self seed was collected from 30 primary transformants and from 20 to 100 seeds per family were sown in the greenhouse. Progeny were visually scored for phenotype aberrations, and four families with interesting phenotypic variants were selected for the molecular analysis described here. These four lines are 88-01, segregating for a round leaf shape (rlm); 88-08, segregating for a variegated leaf chlorosis (var); 88-14, for a lethal albino mutation (lab) and 88-94, containing a mutation resulting in both chlorosis of the leaves as well as an entire leaf shape (bzr). Three of these mutants (88-01, 88-08, 88-14) segregated in the $F_1$ progeny in ratios consistent with being simple monogenic recessive mutations. The fourth, 88-94, appeared only once in about 50 seedlings. In order to get a general picture of the behavior of Ac in transgenic progeny, we also characterized the segregation of Ac in six families which appeared phenotypically normal. These ten families are listed in Table 2 below.

TABLE 2

Summary of $F_1$ Southern blot data

| Family | Phenotype | No. progeny | No. copies Ac T-DNA | Ac T-DNA | — | — Progeny inheriting T-DNA | — a transposed Ac |
|---|---|---|---|---|---|---|---|
| 88-01 | rm | 17 | 1 | 12 | 2 | 3 | 0 | 12 |
| 88-04 | wt | 6 | 1 | 4 | 0 | 2 | 0 | 0 |
| 88-06 | wt | 6 | 1 | 4 | 1 | 1 | 0 | 1 |
| 88-08 | var | 12 | >2 | 0 | 0 | 9 | 3 | 0 |
| 88-09 | wt | 6 | >2 | 6 | 0 | 0 | 0 | 0 |
| 88-10 | wt | 6 | 1 | 2 | 0 | 1 | 3 | 2 |
| 88-11 | wt | 6 | 1 | 5 | 0 | 0 | 1 | 0 |
| 88-12 | wt | 6 | >1 | 2 | 1 | 2 | 1 | 1 |
| 88-14 | lab | 12 | 4 | 10 | 1 | 0 | 1 | 5 |
| 88-94 | bzr | 13 | 1 | 7 | 1 | 3 | 2 | 5 |
| Total | | 90 | | 52 | 6 | 21 | 11 | 26 |

Southern hybridizations were made of the 6 to 17 progeny of the ten selected primary transformants as described above, with the results set forth in Table 2. We distinguished Ac insertions which were genetically transmitted from those that occurred somatically in the $F_1$ by three criteria: the same insertion was detected in both parental and progeny plants; the same insertion comigrated in at least two siblings; or a meiotic recombination event was detected that resulted in progeny containing a transposed Ac element but no T-DNA.

The presence of a transposed Ac in a progeny devoid of T-DNA sequences indicates that a transposed Ac was inherited from the parent. Such occurrences require that Ac transpose away from the T-DNA locus in the parent. This then allows recombination and assortment of the two loci. Therefore an Ac inherited without T-DNA had to have transposed first in the parent. To score the progeny for the presence of Ac and T-DNA sequences, a HindIII-BamHI blot was probed sequentially with the 4.3-kb Ac probe and the wx probe. This digestion allowed the detection of Ac sequences irrespective of their location thanks to the internal 1.6-kb doublet which hybridizes with the Ac probe. The wx probe detected either a 2.4-kb resident band or a 3.0-kb empty donor site. The blots were further probed with T-DNA right and left border-specific probes to determine the number of copies of pMAC in the transformants. Every progeny which contained wx sequences, either as a resident or an empty donor site fragment, also contained T-DNA border sequences. Therefore, the presence of the wx revertant band, pMAC resident band, or T-DNA borders could be used to identify the T-DNA insertion locus.

One plant had Ac sequences but no wx or T-DNA sequences. The pattern observed in this plant must have arisen from meiotic recombination between the transposed Ac and the donor pMAC plasmid. The frequency of this event in the nine other families examined is described later.

One plant from family 88-14, plant I, had a single new Ac insertion as determined by using each of the two Ac probes. Unlike the other progeny, there were no resident pMAC fragments of 2.4 kb and 3.6 kb in this plant. Additionally, there was no evidence of the donor plasmid in this progeny when the blot was probed with either wx- or T-DNA-specific probes.

Data obtained by probing Southern blots of the 10 families with Ac, wx and T-DNA border probes is summarized in Table 2. This table indicates the number of progeny with both Ac and T-DNA sequences, the number with either Ac or T-DNA sequences, and the number with neither. In five out of ten families, progeny were identified that contained Ac but not donor plasmid sequences. This means that in at least one-half the families, some progeny inherited an Ac that transposed a sufficient genetic distance to allow detection of recombination. In total, 6 out of 90 progeny had Ac but no T-DNA. This is an underestimate of the number of progeny in which Ac and T-DNA meiotically assort because even when the sequences are totally unlinked, 9/16 of the progeny will still contain both. Due to the small population sizes, we were not able to estimate map distances of transposition.

Progeny plants which contain a single transposed copy of Ac which has meiotically segregated from the T-DNA are valuable for following subsequent behavior of Ac. Progeny plant 88-01 O is such a candidate. We sowed self seed from this plant and isolated DNA from seven progeny. The DNA was digested with HindIII and the resultant Southern hybridization probed with the entire Ac sequence found on pJAC-D. Digestion with Hind III of the transposed element in 88-01 O results in one internal fragment of 1.6 kb and junction fragments of 2.2 kb and 3.7 kb. Due to segregation, two of the seven progeny,(A and F) did not inherit an Ac. The five progeny that harbor Ac (B, C, D, E and G) show the same three bands that were present in the parent. However, in addition to these parental bands, new Ac insertion sites are apparent. The varying intensities of these bands suggests strongly that they result from somatic transposition of Ac in the $F_2$. Progeny of two other $F_1$ plants which contained a single copy of Ac and no T-DNA (88-01 C and 88-14 I) also exhibited somatic transposition of Ac in the $F_2$ generation. We therefore conclude that Ac continues to transpose at least up to the third generation following regeneration.

III. Insertion of the Insect Control Protein Gene From *Bacillus thuringiensis* var. *kurstaki* Into Tomato Using the Transformation Vector pTV101

The bacteria *Bacillus thuringiensis* var. *kurstaki* (*B.t.k.*) encodes a protein (*B.t.* protein) which is preferentially lethal to lepidopteran insects. The gene encoding this protein has been cloned, DNA sequences which allow expression of the gene implants have been inserted at the control sequence of the gene, and the gene transformed into tomato plants by Agrobacterium-mediated transformation (Fischoff, D. et al. *Bio/technology* 5:807–813 (1987), incorporated by reference herein). Plants which express this chimeric protein show increased tolerance to lepidopteran larvae.

A. Cloning the *B.t.k.* Gene Into pTV101

The approximately 4 kb DNA fragment containing the *B.t.k.* toxin gene linked to the CaMV35S promoter and NOS3' regulatory sequences are digested from the plasmid pMON9711 using the appropriate restriction enzymes. This fragment is then cloned into the Ds portion of pTV101 using any of the available restriction enzymes in the polylinker region. Following confirmation of the predicted structure by electrophoresis through agarose gels, the vector is introduced into *Agrobacterium tumefaciens* strains containing disarmed Ti plasmids as described by Fraley et al. *Bio/technology* 3:629–635 (1985). The final construction of pBT101 is diagrammed in FIG. 6.

The Agrobacterium containing pBT101 is incubated with cotyledon extracts of the tomato cultivars as described in Yoder et al. (1988), supra. Transformed cells are selected for by including 50 μg/ml kanamycin in the regeneration media. Tomato plants are regenerated into mature plants as described (Yoder, supra (1988)). Genomic DNA is assayed by Southern hybridization to confirm the desired T-DNA insertion.

During the regeneration of the primary transformant bearing a pBT101, the Ds portion of the construction transposes to a new genomic location catalyzed by the transposase gene. The Ds portion bearing the *B.t.k.* gene may transpose more than one time during the growth of the plant. Indeed, it has been observed that different parts of the same primary transformant will contain transposed elements at different genomic locations, indicative of secondary transposition events (Yoder et al. (1988)).

When the plant is mature, it is either self-pollinated or outcrossed to a sexually compatible variety. Progeny $F_1$ are the hybrid progeny of a cross or by selfing the primary $R_0$ transformant seed are collected and progeny plants grown.

When the Ds bearing the *B.t.k.* gene has transposed to a chromosomal location genetically distant from the donor vector pBT101 insertion site, the chimeric Ds and the pBT101 donor vector, now devoid of Ds, will independently assort in the progeny. In the case of the backcross, one-half the $F_1$ progeny will contain pBT101 sequences and one-half will contain the DS gene. Since each is randomly distributed in this population, approximately ¼ of the progeny will contain pBT101 and Ds, ¼ will contain pBT101 but no Ds, ¼ will contain Ds but no pBT101, and ¼ will contain neither. A different ratio is obtained when the $R_0$ plant is self-pollinated, in this case the number of plants containing both pBT101, and Ds, pBT101 but no Ds, Ds but no pBT101, or neither pBT101 or Ds, will be 9:3:3:1. In both cases, a certain proportion of the plants will contain a Ds sequence bearing the *B.t.k.* gene but do not contain any other sequences contributed by the donor plasmid. The Ds-*B.t.k.* portion is now stable because the transposase gene has been eliminated along with the rest of the donor sequences.

B. Cloning the *B.t.k.* Gene-Ds Construction and the Transposase Sequences on Separate Plasmids An alternative scheme for moving a *B.t.k.* gene-Ds construction from its original location is to introduce the transposase gene on a separate plasmid. This has the advantage that a primary transformant containing the gene of interest in a stable location can be regenerated prior to moving the desired gene to a new location.

A construction similar to pDs202 is prepared which contains the *B.t.k.* gene in place of the B-gal fragment. This construction is transformed into a plant and a mature plant regenerated. Unlike the previous case, the Ds-*B.t.k.* portion is now completely stable because no transposase gene has been introduced into the plant.

An active transposase gene can be introduced into the plant containing the Ds-*B.t.k.* construction in either of two ways. First, the transposase gene can be directly transformed into the primary transformant or into progeny of this plant. For example, the primary transformant containing the Ds-*B.t.k.* construction would be grown to maturity, self-pollinated, and seed collected. These seed would be germinated and emerging seedlings used as host material for a secondary transformation using a plasmid containing the transposase gene. In some cases, it may be beneficial to use a second selectable marker, e.g., hygromycin resistance, to identify transformants containing transposase. The transgenic plants which contain both the Ds-*B.t.k.* construct and the transposase gene are grown to maturity, self-pollinated or backcrossed, and progeny seed collected. As in the previous scheme, plants containing a transposed Ds-*B.t.k.* fragment but no other donor sequences can be identified as segregating in the progeny populations.

C. Removal of Undesired Genes From a Transforming DNA Construction

In some cases, it may not be desirable to move the gene of interest away from its original insertion site following transformation. This will be the case if expression of the desired gene is optimal in its initial location. In these cases, repositioning of the gene of interest may decrease the efficiency with which the gene is expressed.

The transposition vector system can be incorporated in these cases by inserting the selectable marker gene between the Ds borders. The *B.t.k.* gene is then cloned into a region of the vector which is not mobilized by the action of transposase. Such a construction is diagrammed in FIG. 7 as pBT201.

The plasmid pBT201 is transformed into a plant and selection for transformants utilizes the kanamycin resistance marker. During the regeneration of this plant, the Ds portion, bearing the selectable marker used for transformation will transpose to new locations. As with the previous cases, when the Ds element has transposed to an unlinked location, segregation of the donor plasmid, bearing the *B.t.k.* gene, and the Ds element, bearing the selectable marker, will result in plants containing the *B.t.k.* gene but no selectable marker sequences.

This scheme can also incorporate the two plasmid system described in section B.

D. Selection of Plants Containing the Gene of Interest But No Undesirable Sequences In each of the schemes described, genetic segregation is used to create plants which contain the desired gene but do not have undesirable sequences. These plants can be readily identified by any of a number of standard diagnostic procedures for identifying foreign DNA in plants. Additionally, low stringency selective conditions can be used to identify plants which do not contain the selectable marker. These conditions are not lethal to plants without the gene (Weide, et al., supra).

IV. Demonstration that a Selectable Marker Inserted Within a Ds Element May be Removed from a Transgenic Plant While Retaining a Gene of Interest.

A. Vector Construction, Transformation and Analysis of Plants.

1. Vector Construction and Transformation.

Vector construction was carried out essentially as described above, leading to the plant transformation constructs depicted in FIG. 8 and FIG. 9. Transformation and analysis of the transformed plants was performed as described above, except that pVCY1647 had its transposase function supplied in trans. Analysis of transformed plant cells was carried out as described above.

2. Self-Cross of T164-1.

The transformant T164-1 was generated using the protocol described above and the transformation vector pVCY1605 (FIG. 8). T164-1 was self pollinated and 87 resulting seedlings were screened for GUS activity and for the presence or absence of T DNA sequences. Using standard techniques, DNA isolated from the seedlings was digested with HindIII, blotted and probed with fragments corresponding to the GUS region, the NPTII coding sequence, the transposase sequences, and both the left and right T DNA borders.

Sixty four progeny contained the Ds-GUS gene. Some of these plants had an intact VCY1605 insertion, indicating that the Ds element did not mobilize in this group. In other plants, the Ds had excised but co-segregated in the progeny with the ancillary T DNA. Of the 87 seedlings examined, 3 contained NPTII, transposase, and the two border sequences but not the Ds-GUS gene. In these transformants the Ds gene had either excised and not reintegrated, or it had reintegrated into a site unlinked to the T DNA and was lost in the progeny through segregation. In either case, the final product was a transgenic plant containing all of the sequences within the T DNA except for the Ds elements and the GUS marker. These progeny demonstrate that a marker gene can be removed from a transgenic plant while retaining a gene of interest residing on the T DNA.

3. Use of A Transformation Vector Containing NPTII Inside of The Ds Transposition Element.

The pVCY1647 vector was introduced into tomato plants as described above. The plants transformed with pVCY1647 (FIG. 9) are then used to generate $F_1$ plants lacking selectable markers. The plants containing both Ds and transposase are either self-pollinated or out-crossed and the progeny scored for the loss of the selectable marker. Following independent segregation, the Ds element and transposase gene are selected out of subsequent plant generations.

What is claimed is:

1. A transgenic plant, which contains a gene of interest and that does not contain foreign ancillary nucleic acids, which foreign ancillary nucleic acids comprise a plant transposon element and those sequences within the transposon element, produced by a method comprising:

(a) transforming a plant with a gene of interest by introduction of the gene on a DNA construct comprising the transposon element, wherein the gene is outside the transposon element;

(b) introducing a transposase gene into the plant;

(c) crossing the transformed plant through self-crossing or with another plant to obtain F1 or more removed generation progeny; and (d) selecting those progeny that carry the gene of interest and are free of the ancillary nucleic acids.

2. A seed derived from a plant of claim 1.

3. The transgenic plant of claim 1 wherein the gene of interest is *B.t.k.*

* * * * *